United States Patent [19]
Fujita et al.

[11] Patent Number: 5,101,019
[45] Date of Patent: Mar. 31, 1992

[54] METHOD FOR REMOVING PERTUSSIS ENDOTOXIN, A PERTUSSIS TOXOID AND ITS PRODUCTION

[75] Inventors: Isao Fujita; Hideo Watanabe; Masatoshi Miyamoto, all of Yamaguchi, Japan

[73] Assignee: Takeda Chemical Industries, Ltd., Osaka, Japan

[21] Appl. No.: 194,216

[22] Filed: May 16, 1988

[30] Foreign Application Priority Data

May 22, 1987 [JP] Japan ................... 62-126394

[51] Int. Cl.$^5$ .............. C07K 3/24; C07K 3/28; A61K 39/10; C12P 21/02
[52] U.S. Cl. ....................... 530/420; 424/92; 435/71.3
[58] Field of Search ......... 435/71.2, 71.3, 74; 424/92, 87, 88; 514/25; 530/350, 420

[56] References Cited

U.S. PATENT DOCUMENTS

| | | | |
|---|---|---|---|
| 3,608,071 | 9/1971 | Relyveld et al. | 424/92 X |
| 3,978,209 | 8/1976 | Limjuco et al. | 424/92 |
| 4,220,717 | 9/1980 | Kuo | 435/101 |
| 4,705,686 | 11/1987 | Scott et al. | 424/92 |
| 4,849,358 | 7/1989 | Chazono et al. | 435/252 |

FOREIGN PATENT DOCUMENTS

| | | | |
|---|---|---|---|
| 0047802 | 3/1982 | European Pat. Off. | 435/69.1 |
| 342149 | 4/1956 | Japan . | |

OTHER PUBLICATIONS

Sofer, G. 1984, Bio/Technology vol. 2, pp. 1035–1038.
Work, E. 1971, "Production, Chemistry, and Properties of Bacterial Pyrogens and Endotoxins", *CIBA Foundation Symposium Pyrogens and Fever*, eds. Wolstenholme, G. E. W. et al., Churchill Livingston, Edinburgh, Scotland, pp. 23–47.
Knox, K. W. et al., 1967, "An Extracellular Lipopolysaccharide-Phospholipid-Protein Complex . . . ", *Biochem. J.*, vol. 103, pp. 192–201.
Watanabe, H. et al., 1983, "An Improvement in the Method of Purification of B. Pertussis LPF-HA Ca Pertussis Toxin and F-HA and a Method (PHA) for Assay of Their Antibodies", *Japanese Journal of Bacteriology*, vol. 38 (1) p. 423.
Hideo Watanabe et al., Japanese Journal of Bacteriology, 38 (1), 423 (1983).

*Primary Examiner*—Richard A. Schwartz
*Assistant Examiner*—Mary E. Mosher
*Attorney, Agent, or Firm*—Wegner, Cantor, Mueller & Player

[57] ABSTRACT

The present invention provides a clear and efficient pertussis endotoxin-removing method characterized in that a fluid containing the antiinfective fraction and endotoxin of strains of phase I *Bordetella pertussis* is supplied with calcium ion in the presence of excess phosphate ion prior to zonal centrifugation and also a pertussis toxoid whose endotoxin content per 10 $\mu$g of proteinic nitrogen is not more than 0.5 ng and its production method.

13 Claims, 2 Drawing Sheets

METHOD FOR REMOVING PERTUSSIS ENDOTOXIN, A PERTUSSIS TOXOID AND ITS PRODUCTION

BACKGROUND AND PRIOR ART

The present invention relates to a method of removing pertussis endotoxin, a pertussis toxoid, and a method of producing the same.

Pertussis is a contagious infectious disease due to *Bordetella pertussis* and runs a serious course in infants and small children.

For the prevention of this disease, vaccines have heretofore been used. However, any vaccine prepared by using the whole organisms of *B. pertussis* produces intense adverse reactions such as fever and, to overcome this disadvantage, an acellular pertussis vaccine (ACP vaccine) substantially free of endotoxin (ET), which is mainly responsible for fever and other adverse reactions, by isolating the antiinfective fraction (hereinafter referred to sometimes as protective fraction) such as filamentous hemagglutinin (FHA), pertussis toxin (PT) and fimbriae has been developed and used.

The most crucial step in the production of an ACP vaccine is the separation of endotoxin (ET) from the antiinfective fraction and generally sucrose-gradient centrifugation has been utilized for this purpose (Japanese Unexamined Patent Publication No. 57-50925 which corresponds to EPC Publication No. 0047802).

Furthermore, as a technique for the removal of pyrogen, the method using calcium phosphate gel is known (Japanese Patent Publication No. 34-2149). It is also known that hydroxylapatite gel, a stabilized version of calcium phosphate gel, is effective in the separation of filamentous hemaggutinin (FHA) from pertussis toxin (PT) and that a substantially endotoxin free filamentous hemagglutinin can be separated from the pertussis toxin by chromatography on hydroxylapatite gel and further purification by affinity chromatography and sucrose-gradient centrifugation (Japanese Journal of Bacteriology, 38 (1), 423, 1983).

Sucrose-gradient centrifugation alone is capable of removing about 99.995% of the endoxin (ET) but as the crude antiinfective fraction-containing fluid is rich in endotoxin (ET), complete separation of the protective fraction from the endotoxin (ET) is hard to achieve and the yield of the antiinfective fraction is accordingly not high. Moreover, since the production volume is small and much cost and time are involved, the method is not satisfactory for commercial purposes.

On the other hand, mere treatment with calcium phosphate gel assures only a low endotoxin elimination rate of about 90 to 99.9% and is, therefore, not useful for practical purposes. It is possible, at the laboratory level, to separate and purify the filamentous hemagglutinin (FHA) fairly free of endotoxin in isolation from the pertussis toxin (PT) by a combination of hydroxylapatite column chromatography, affinity chromatography and sucrose-gradient centrifugation, but the method does not assure a commercially useful output. Furthermore, the technology involved is different in objective from the present invention which is directed to the removal of endotoxin (ET) from a fluid containing the protective fraction and endotoxin (ET).

Against the above technical background, we sought an efficient method for removing the endotoxin (ET) and found that a calcium phosphate gel treatment preceding the sucrose-gradient centrifugation results in a very neat separation of the protective fraction from endotoxin (ET) and, furthermore, affords improvements in both the volume of production and the rate of removal of endotoxin (ET) over sucrose-density centrifugation. These findings were followed by further research, which culminated in the completion of the present invention.

BRIEF SUMMARY OF THE INVENTION

The present invention is therefore directed to (1) a method of removing endotoxin from a fluid containing the antiinfective fraction and endotoxin of strains of phase I *Bordetella pertussis* by zonal centrifugation characterized in that said fluid is supplied with calcium ion in the presence of excess phosphate ion prior to the zonal centrifugation and the resulting precipitate is discarded; (2) a method of producing a pertussis toxoid characterized by detoxifying an antiinfective fraction-containing fluid obtained by the above method and (3) a pertussis toxoid whose endotoxin content per 10 $\mu$g of proteinic nitrogen is not more than 0.5 ng.

By the pertussis endotoxin-removing method of the present invention, the separation of the antiinfective fraction from the endotoxin can be made more certain and neat, with the result that the protective fraction can be easily isolated in improved yield. Furthermore, since a large volume of starting material can be subjected to zonal centrigufation, the output of pertussis toxoid can be more than doubled, with the endotoxin being removed with a high efficiency. Therefore, the industrial value of the present invention is significant.

Furthermore, the endotoxin content of the pertussis toxoid according to the present invention is less than one-tenth of that of the conventional toxoid; the use of the pertussis toxoid of the invention enables the industry to manufacture vaccines possessing the same immunological potency as the conventional vaccines but of reduced toxicity.

DETAILED DESCRIPTION

The aforesaid fluid containing the antiinfective fraction and endotoxin of strains of phase I *Bordetella pertussis* may, for example, be the supernatant of a culture broth obtainable by growing strains of phase I *B. pertussis* or a concentrate thereof, and the concentrate is particularly preferred. Culture of strains of phase I *Bordetella pertussis* can be conducted in the conventional manner. Thus, for example, the organisms are grown in a broth medium (such as Cohen-Wheeler medium or Stainer-Scholte medium) at about 35°-37° C. for about 5-7 days. The supernatant of a culture broth thus obtained is collected, for example, by filtration or centrifugation. This supernatant can be subjected directly, or after concentration, to the next step for removal of endotoxin. The concentration for this purpose can be effected by utilizing a per se known salting-out technique. For example, 2 to 5 kg of ammonium sulfate is added to each 10 l of the culture supernatant and the resulting precipitate is collected, for example, by filtration or centrifugation. This precipitate is then dissolved in an appropriate amount of 1M sodium chloride-0.05M phosphate buffer and the solution is centrifuged or otherwise treated to separate the supernatant.

The removal of endotoxin in accordance with the present invention comprises supplying a fluid containing the antiinfective fraction and endotoxin of strains of Phase I *Bordetella pertussis* with calcium ion in the presence of an excess of phosphate ion, discarding the resulting precipitate, and subjecting the mother fluid to zonal centrifugation.

If phosphate ion is not present in the material fluid, a phosphate buffer solution such as, for example, 0.05M phosphate buffer supplemented with 1M sodium chloride is added to the fluid and, then, calcium ion is supplied. The calcium ion to be supplied may be any of such soluble calcium salts as calcium acetate, calcium chloride, calcium nitrate, etc. and insoluble calcium salts such as calcium phosphate etc. Particularly preferred are calcium acetate and calcium chloride.

The ratio of phosphate ion to calcium ion is about 1.25 to 30 equivalents, Preferably about 1.5 to 7.5 equivalents, of phosphate ion to each equivalent of calcium ion, and it is recommended to ensure that about 0.01 to 0.1 milliequivalent/ml, preferably about 0.02 to 0.07 milliequivalent, of calcium phosphate gel is formed.

A typical procedure is as follows. Assuming that when the precipitate obtained by fractional precipitation of the supernatant of a culture broth of strains of phase I Bordetella pertussis using ammonium sulfate is dissolved in 1M sodium chloride-0.05M phosphate buffer, calcium acetate is added at the final concentration of about 0.1 to 1.0 w/v %, preferably about 0.2 to 0.6 w/v %, ar a pH about 6.5-9 and the mixture is allowed to react gradually at about 4° C. to room temperature for about 20 minutes to 2 hours to give a calcium phosphate gel. After this reaction, the resulting precipitate is removed by a per se known method such as filtration or centrifugation. By this procedure, about 90 to 99.9% of the endotoxin can be selectively removed without any appreciable loss of the protective fraction.

The semi-crude product obtained as above is further subjected to zonal centrifugation, preferably after further concentration by ammonium sulfate salting (fractional precipitation).

The zonal centrifugation according to the invention may be any of sucrose-gradient centrifugation, potassium tartrate-density centrifugation, cesium chloride-gradient centrifugation, etc., although sucrose-gradient centrifugation is particularly preferred. The usual conditions of sucrose-gradient centrifugation are : density gradient: 0-30w/w%; Rmax: ca 60,000-122,000 G; time: ca 10-24 hr.

In accordance with the present invention, the thus-obtained fluid containing the pertussis antiinfective fraction is detoxified with formalin, glutaraldehyde, pyruvaldehyde or the like and, then, the excess of formalin, glutaraldehyde, pyruvaldehyde or the like is removed by a per se known procedure such as dialysis, centrifugation or ultrafiltration, etc. to give a pertussis toxoid. A recommended exemplary detoxication procedure comprises, as described in Japanese Unexamined Patent Publication No. 57-50925, adding formalin to a pertussis antiinfective fraction-containing fluid at the level of about 0.1-0.6 v/v % in substantial absence (i.e. not more than 10 mM) of basic amino acids (for example, L-lysine, glycine, etc.), incubating the mixture at about 32-42° C. for about 3-14 days to cause flocculation, disrupting the flocculent toxoid by a suitable means (e.g. ultrasonication at about 10-50 kilocycles), and suspending the same in an appropriate aqueous medium (for example, M/100-M/250 phosphate buffered saline) to give a toxoid fluid.

In accordance with the present invention, there can be produced a pertussis toxoid whose endotoxin content per 10 μg of proteinic nitrogen is not more than 0.5 ng, preferably not more than 0.1 ng, as determined by limulus lysate test. In other words, the endotoxin elimination rate can be improved to not less than 99.9994% or preferably to at least 99.9998%.

The pertussis toxoid according to the present invention can be processed by the established procedure into a precipitated pertussis vaccine or a precipitated pertussis-diphtheria-tetanus triple vaccine for vaccination of humans.

EXAMPLE

Figure 1:
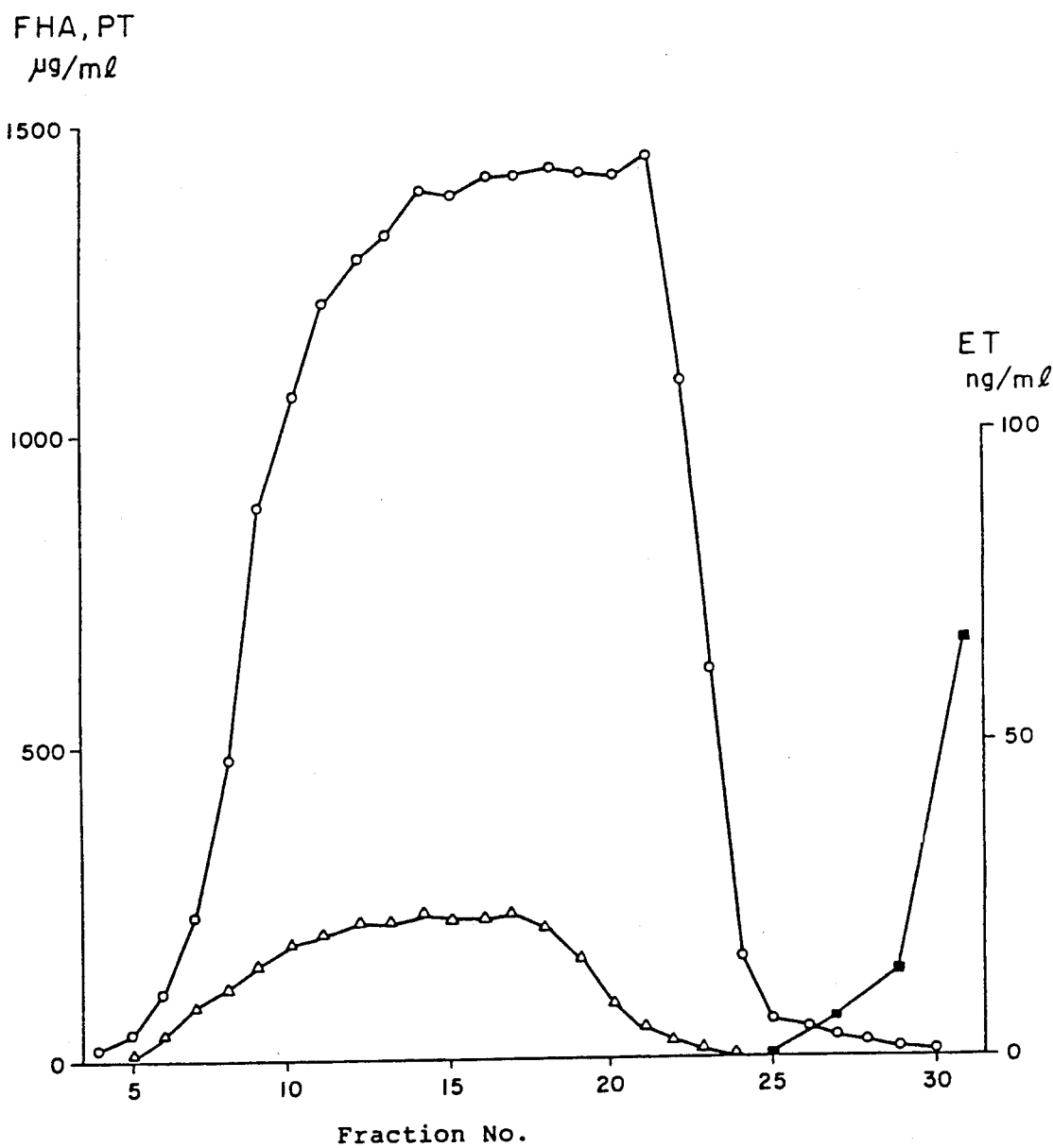
FIGS. 1 and 2 show the sucrose-gradient centrifugation profiles of the calcium phosphate gelation group and control group, respectively, in Example 1.

The following reference and working examples are further illustrative but by no means limitative of the invention.

The properties of Bordetella pertussis Tohama phase I strain employed in the following Examples and Reference Examples are disclosed in e.g. Infection and Immunity,6,899 (1972). This strain has been maintained at National Institute of Health, Tokyo, Japan (NIHJ), and deposited also at Institute for Fermentation, Osaka, Japan under the accession number of IFO 14073 since Aug. 13, 1980.

REFERENCED EXAMPLE 1

Bordetella pertussis Tohama Phase I strain (IFO 14073) was inoculated onto Bordet-Gengou medium prepared from potato, peptone, sodium chloride, agar, and bovine blood and incubated at 35° C. for 5 days. Then, translucent circular colonies were picked and one reacting to K agglutinin antibody was spread again on Bordet-Gengou medium to prepare a seed culture. Then, this seed culture was transplated in Cohen-Wheeler medium and incubated at 35° C. for 1 day. The resulting bacterial suspension was added to Stainer-Scholte medium at the final concentration of about 1 billion cells/ml and, using a Roux bottle, was incubated at 35° C. for 5 days. The culture broth was harvested and about 20w/v % of ammonium sulfate was added to the supernatant. After thorough mixing, the mixture was allowed to stand at 4° C. After about 14 days, the mixture was centrifuged, the supernatant was discarded and the sediment was harvested. Then, one-tenth volume, based on the solution collected, of 1M sodium chloride-0.05M phosphate buffer (pH 8.0) was added to the sediment and the mixture was stirred well and allowed to stand at 4° C. for 4 days. The mixture was then centrifuged again and the supernatant (extract I) was collected. This extract I was rich in the protective fraction containing filamentous hemagglutinin (FHA) and pertussis toxin (PT) as well as endotoxin but was free of cells.

To aliquots of this extract I was gradually added calcium acetate at the final concentrations of 0, 0.2, 0.4, 0.6, 0.8, and 1.0 w/v % and each mixture was gently stirred at room temperature for about 1 hour. Then, the resulting precipitate was filtered off using a filter paper to give a supernatant. Using each of the supernatants thus obtained, chick hemagglutinin (HA) titer, PT content and ET content were determined. The results are shown in Table 1. The PT content was assayed by ELISA and the ET content was assayed by the limulus lysate method (Mallinckrodt kit) using *E. coli* endotoxin (Difco 055-B5) as the standard.

It is clear from Table 1 that ET can be selectively eliminated by the steps of supplying the calcium salt in the presence of an excess of phosphate ion and discarding the precipitate. Moreover, by adding 0.2 to 0.6w/v % of calcium acetate, about 99% of the ET can be removed without incurring a loss of the protective fraction (HA titer and PT content).

TABLE 1

| Level of calcium acetate added (w/v %) | Endotoxin content (ng/ml) | Removal of endotoxin (%) | HA titer* (HAu/ml) | PT content (Eu/ml) |
| --- | --- | --- | --- | --- |
| 0 | 87,800 | — | 1200 | 1220 |
| 0.2 | 1,043 | 98.2 | 1100 | 1140 |
| 0.4 | 960 | 98.9 | 1400 | 1400 |
| 0.6 | 720 | 99.2 | 1200 | 1080 |
| 0.8 | 78 | 99.9 | 400 | 1210 |
| 1.0 | <20 | >99.9 | <200 | 1030 |

*The HA titer predominantly reflects the FHA content.

REFERENCE EXAMPLE 2

The procedure of Reference Example 1 was repeated except that the pH was adjusted to 5.0–10.0 with sodium hydroxide or hydrochloric acid and the level of addition of calcium acetate was set at 0.5 w/v %. The results are shown in Table 2.

Beginning at pH 6.0, gelation took place and the removal of endotoxin increased with increasing pH. It is apparent from Table 2 that the optimal pH is 7–9.

TABLE 2

| pH | Endotoxin content (ng/ml) | Removal of endotoxin (%) | HA titer* (HAu/ml) |
| --- | --- | --- | --- |
| (before treatment) | 334,000 | — | 3,000 |
| 5.0 | 195,000 | 41.6 | 2,700 |
| 6.0 | 108,000 | 67.7 | 3,000 |
| 6.5 | 53,000 | 84.1 | 3,000 |
| 7.0 | 24,000 | 92.8 | 3,000 |
| 8.0 | 22,000 | 93.4 | 3,200 |
| 9.0 | 18,000 | 94.6 | 3,000 |
| 10.0 | 268,000 | 19.8 | 3,000 |

REFERENCE EXAMPLE 3

The procedure of Reference Example 2 was repeated except that 5 w/v % of hydroxy lapatite (BDH) was used in lieu of 0.5 w/v % of calcium acetate. The results are shown in Table 3.

It is clear from Table 3 that compared with the addition of calcium acetate for the formation of calcium phosphate gels within the solution, the addition of hydroxylapatite provides a less efficient removal of endotoxin and shows the reverse of the above-noted pH dependency.

TABLE 3

| pH | Endotoxin content (ng/ml) | Removal of endotoxin (%) | HA titer* (HAu/ml) |
| --- | --- | --- | --- |
| (before treatment) | 334,000 | — | 3,000 |
| 6.0 | 160,000 | 52.1 | 3,000 |
| 7.0 | 195,000 | 41.6 | 3,000 |
| 8.0 | 264,000 | 21.0 | 3,000 |
| 9.0 | 294,000 | 12.0 | 3,000 |

EXAMPLE 1

Figure 2:
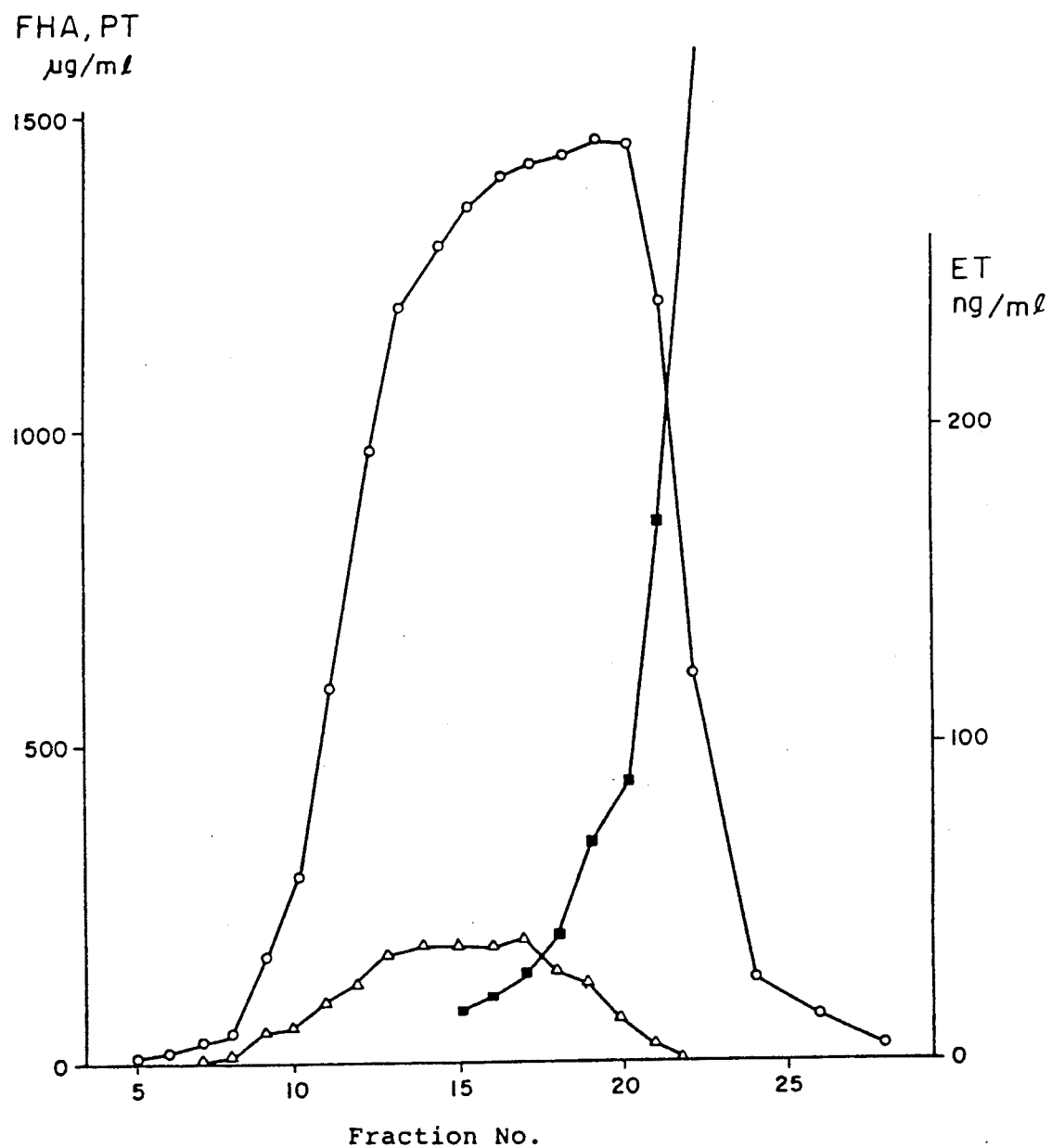

Each of Extract I (control group) obtained by the procedure described in Reference Example 1 and the material obtained by adding calcium acetate to Extract I at the final concentration of 0.5 w/v % and thereafter treating the mixture as described in Reference Example 1 was mixed with an equal volume of a saturated aqueous solution of ammonium sulfate and the mixture was allowed to stand at 4° C. for seven days. This ammonium sulfate-precipitated material was centrifuged at 10,000 rpm for 20 minutes and the sediment was collected. Then, about 1/300 volume, based on the volume of the solution, of 1M sodium chloride-0.05M phosphate buffer (pH 8.0) was added. After thorough stirring, the mixture was dialyzed in a tube using 1M sodium chloride solution (pH 8.0) as the external fluid. The dialyzate was subjected to sucrose-gradient centrifugation under the conditions of sucrose density gradient = 1-30 w/w%, Rmax = 69,400 G and time = ca 18 hr. The load for the calcium phosphate gelation group was doubled over the load for the control group. After centrifugation, 34 w/w% sucrose solution was fed into the rotor for fractional harvest. Each fraction so collected was determined for FHA and PT content by ELISA and for ET content by the same method as described in Reference Example 1. The results are shown in FIGS. 1 and 2. In the curves, FHA, PT and ET contents are designated by -O- -Δ- and -■-, respectively.

It is apparent from FIGS. 1 and 2 that despite the doubling of the load applied, the calcium phosphate gelation group provided a clearly more discrete separation of the protective fraction (FHA, PT) from the endotoxin than did the control group.

In each of the calcium phosphate group and the control group, the fraction lean in ET and rich in FHA was collected and its proteinic nitrogen content was adjusted to about 50 μg/ml. To this were added 0.02 w/v % of gelatin, 0.05 v/v % of Tween 80 and 0.4 v/v % of formalin and the mixture was incubated at 39° C. for seven days. The resulting toxoid fluid was dialyzed and determined for ET. The results are shown in Table 4. The ET content was assayed by the limulus lysate test (Wako Pure Chemical kit) using *E. coli* endotoxin (Difco 055-B5) as the standard. It is clear from Table 4 that when compared for the ET content of pertussis toxoid stock fluid at the vaccine level (proteinic nitrogen content 10 μg/ml), the ET content in the calcium phosphate gelation group has been improved to less than 1/40 of that in the control group.

| | Ca phosphate gelation group | | Control group | |
| --- | --- | --- | --- | --- |
| | Endotoxin content | Removal of endotoxin | Endotoxin content | Removal of endotoxin |
| Exp. 1 | 0.3 ng/ml (0.06 ng/ml) | 99.99994% | 19.0 ng/ml (3.8 ng/ml) | 99.99591% |
| Exp. | 0.3 ng/ml | 99.99988% | 12.8 ng/ml | 99.99458% |

-continued

| | Ca phosphate gelation group | | Control group | |
|---|---|---|---|---|
| | Endotoxin content | Removal of endotoxin | Endotoxin content | Removal of endotoxin |
| 2 | (0.06 ng/ml) | | (2.6 ng/ml) | |

*The figure in parentheses represents the endotoxin content per 10 μg/ml of proteinic nitrogen.

EXAMPLE 2

According to the original method of Levine (Reo Levine, Joseph L. Stone & Louise Wyman: Factors affecting the efficiency of the aluminum adjuvant in diphtheria and tetanus toxoids. J. Immunology 75, 307-307, 1955), each of 2 batches of pertussis toxoid stock fluid was diluted with M/250 phosphate buffered saline (pH 7.0) to give a proteinic nitrogen content of about 10 μg/ml, followed by addition of aluminum chloride at the final concentration of 0.18 w/v %. The mixture was stirred well and adjusted to pH 7.0 with hydrochloric acid or sodium hydroxide to prepare about 0.2 mg/l of aluminum-adsorbed vaccine.

The principal properties of this vaccine were: pH 7.0, rabbit pyrogenicity: negative, mouse weight reduction: 10 BWDU/ml or less, mouse leukocyte increase: 0.5 LPU/ml or less, mouse histamine sensitization: 0.8 HSU/ml or less, and pertussis toxoid potency: 8 IU/ml or more. Thus, both batches met the standard values specified in the Standard of Biological Products.

What is claimed is:

1. A method for removing endotoxin from a fluid containing the antiinfective fraction and endotoxin of strains of phase I *Bordetella pertussis* by *zonal centrifugation* characterized in that said fluid is supplied with calcium ion in the presence of excess phosphate ion prior to the zonal centrifugation and the resulting precipitate is discarded.

2. A method according to claim 1, wherein a ratio of phosphate ion to calcium ion is about 1.25 to 30 equivalents of phosphate ion to each equivalent of calcium ion.

3. A method according to claim 2, wherein the ratio is about 1.5 to 7.5 equivalents of phosphate ion to each equivalent of calcium ion.

4. A method according to claim 1, wherein the calcium ion to be supplied is a calcium ion of calcium acetate or calcium chloride.

5. A method according to claim 1, wherein the resulting precipitate is about 0.01 to 0.1 milliequivalent of calcium phosphate gel relative to 1 of solution.

6. A method according to claim 1, wherein the resulting precipitate is about 0.02 to 0.7 milliequivalent of calcium phosphate gel relative to 1 ml of solution.

7. A method according to claim 1, wherein the resulting precipitate is formed at a temperature in the range of about 4° C. to room temperature and the pH value in the range of from about 6.5 to 9 for about 20 minutes to 2 hours.

8. A method according to claim 1, wherein the resulting precipitate is calcium phosphate gel which is produced by dissolving the precipitate obtained by fractional precipitation of the supernatant of a culture broth of strains of phase I *Bordetella pertussis* using ammonium sulfate, in 1M sodium chloride-0.05M phosphate buffer, adding calcium acetate to a final concentration of about 0.1 to 1.0 w/v % to the solution at pH about 6.5 to 9 of the final solution and allowing the mixture to react at about 4° C. to room temperature for about 20 minutes to 2 hours.

9. A method according to claim 8, wherein the final concentration of calcium acetate is about 0.2 to 0.6 w/v %.

10. A method according to claim 1, wherein the zonal centrifugation is sucrose-gradient centrifugation.

11. A method according to claim 10, wherein the sucrose-gradient centrifugation is carried out under the conditions of density gradient: 0 to 30 w/w %; R max: about 60,000 to 122,000G; time: about 10 to 24 hours.

12. A method of producing a pertussis toxoid characterized by detoxifying an antiinfective fraction-containing fluid obtained by the method according to claim 1.

13. A method according to claim 12, which comprises a) dissolving the precipitate, which is obtained by fractional precipitation of the supernatant of a culture broth of strains phase I *Bordetella pertussis* using ammonium sulfate, in 1M sodium chloride-0.05 M phosphate buffer,
b) adding calcium acetate to a final concentration of about 0.2 to 0.6 w/v % to the solution at pH about 6.5 to 9 of the final solution,
c) allowing the mixture to react at about 4° C. to room temperature for about 20 minutes to 2 hours,
d) discarding the resulting calcium phosphate gel, followed by adding formalin to a final concentration of about 0.1 to 0.6 v/v % in substantial absence of basic amino acids to the antiinfective fraction-containing fluid obtained by sucrose-density centrifugation under the conditions of sucrose-gradient: 0 to 30 w/w %; Rmax: about 60,000 to 122,000G; time: about 10 to 24 hours,
e) incubating the mixture at about 32 to 42° C. for about 3 to 14 days to cause flocculation,
f) disrupting the flocculent toxoid, and
g) suspending the same in an aqueous medium.

* * * * *